United States Patent [19]

Letton

[11] Patent Number: 5,312,934

[45] Date of Patent: May 17, 1994

[54] SYNTHESIS OF SULFATED POLYHYDROXY FATTY ACID AMIDE SURFACTANTS

[75] Inventor: James C. Letton, Forest Park, Ohio

[73] Assignee: The Procter & Gamble Company, Cincinnati, Ohio

[21] Appl. No.: 984,067

[22] Filed: Nov. 30, 1992

[51] Int. Cl.$^5$ ............................................. C11D 1/28
[52] U.S. Cl. ................................ 554/98; 554/44; 554/66; 554/68; 554/94
[58] Field of Search ................. 554/66, 98, 49, 50, 554/68, 94, 44

[56] References Cited

U.S. PATENT DOCUMENTS

| | | | |
|---|---|---|---|
| 2,268,443 | 12/1941 | Crowder | 584/98 |
| 2,717,894 | 9/1955 | Schwartz | 584/98 |

*Primary Examiner*—José G. Dees
*Assistant Examiner*—Deborah D. Carr
*Attorney, Agent, or Firm*—Jerry J. Yetter

[57] ABSTRACT

Polyhydroxy fatty acid amide nonionic surfactants are converted in high yields to their sulfated analog surfactants using an $SO_3$/pyridine complex as a sulfating agent. Thus, $C_{12}$–$C_{18}$ N-methyl glucamide is sulfated in methylene chloride or pyridine solvent to form the corresponding sulfated glucamide in yields of 80% or higher.

2 Claims, No Drawings

SYNTHESIS OF SULFATED POLYHYDROXY FATTY ACID AMIDE SURFACTANTS

FIELD OF THE INVENTION

Polyhydroxy fatty acid amide surfactants are sulfated using an $SO_3$/pyridine complex. Higher yields of the desired sulfated product are routinely secured, as compared with the art-disclosed sulfation with chlorosulfonic acid.

BACKGROUND OF THE INVENTION

Most conventional detergent compositions contain mixtures of various detersive surfactants in order to remove a wide variety of soils and stains from surfaces. In particular, various anionic surfactants, especially the alkylbenzene sulfonates, have been employed to remove particulate soils, and various nonionic surfactants, especially the alkyl ethoxylates, have been used for removing greasy soils and stains. Mixtures of such anionic and nonionic surfactants are used in many modern detergent compositions. Unfortunately, many such surfactants are prepared mainly from petrochemical feedstocks.

Considerable attention has lately been directed to nonionic surfactants which can be prepared using mainly renewable resources, such as fatty acid esters and sugars. One such class of surfactants includes the polyhydroxy fatty acid amides. A combination of such amide surfactants with conventional anionic surfactants has also been studied.

It will be appreciated by the skilled chemist that the polyhydroxy fatty acid amides contain multiple hydroxyl groups which are susceptible to conversion into other substituent groups. If such substituent groups were to be anionic in character, the resulting materials would be anionic surfactants. Thus, using a single fatty acid ester/sugar/amine feedstock, it would be possible to prepare not only a polyhydroxy fatty acid amide class of nonionic surfactants, but also anionic surfactant analogs thereof. Thus, the desirable mixtures of nonionic/anionic surfactants would become available from mainly renewable, nonpetrochemical feedstocks.

Sulfated derivatives of polyhydroxy fatty acid amides have been reported in the literature. These materials have been prepared by reacting chlorosulfonic acid or sulfuric acid plus urea with the hydroxyl constituents present in the polyhydroxy fatty acid raw material. However, it has now been determined that the preparation of such sulfated materials with polyhydroxy fatty acid amides using chlorosulfonic acid is non-routine. More particularly, yields of polyhydroxy fatty acid amide sulfate can be as low as 16% using chlorosulfonic. The reason for the low yields is not readily apparent. While not intending to be limited by theory, it may be that the hydrogen chloride which results from the reaction of the hydroxyl substituents with the chlorosulfonic acid can somehow attack the sugar substituent in the polyhydroxy fatty acid amide, thereby reducing overall yields. In any event, while such low yields may be tolerable under situations where a high priced ingredient is being prepared and wherein extensive purification procedures are justified, such is not the case when preparing low cost bulk items such as detersive surfactants.

By the present invention, an improved method for sulfating polyhydroxy fatty acid amides has been devised which uses sulfur trioxide in the form of a pyridine complex. Overall conversion of the polyhydroxy fatty acid amide into the sulfated polyhydroxy fatty acid amide is substantially increased.

BACKGROUND ART

A method for preparing crude polyhydroxy fatty acid amides (glucamides) is described in U.S. Pat. No. 1,985,424, Piggott, and in U.S. Pat. No. 2,703,798, Schwartz. The use of such glucamides with various synthetic anionic surfactants is described in U.S. Pat. No. 2,965,576, corresponding to G.B. Patent 809,060. The sulfuric esters of acylated glucamines and various methods of preparation are disclosed in U.S. Pat. No. 2,717,894, Schwartz. The sulfation of glycoside surfactants is disclosed in Japanese J04005297 92.01.09; Derwent Abstract Accession Number 92-060740/08.

SUMMARY OF THE INVENTION

The present invention encompasses a method for sulfating a polyhydroxy fatty acid amide, comprising contacting said fatty acid amide with an $SO_3$/pyridine complex. Overall yields are typically at least about 80%, by weight. The method is preferably conducted in a non-hydroxy solvent, especially methylene chloride or pyridine. The method is preferably conducted at a reaction temperature from about 25° C. to about 35° C. The resulting yields are at least about 80% by weight and the reaction products are desirably free from cyclized by-products which can be difficult to biodegrade.

A preferred method herein employs a polyhydroxy fatty acid amide which is substantially free of cyclized by-products.

All percentages, ratios and proportions herein are by weight, unless otherwise specified. All documents cited herein are incorporated by reference.

DETAILED DESCRIPTION OF THE INVENTION

The compositions and processes of this invention most preferably employ high quality polyhydroxy fatty acid amide surfactants which are substantially free of cyclized and ester-amide by-products. For high sudsing compositions, especially hand-wash, most especially hand dishwashing where the consumer expects high, persistent suds, the polyhydroxy fatty acid amides preferably should also be substantially free of contamination by residual sources of fatty acids. The following preparative methods afford the desired materials using conventional, mainly renewable resources, and are described herein in some detail, including the optional step of reducing the level of free fatty acids in the primary reaction by minimizing moisture content, and in the reduction of nascent fatty acid levels by means of the secondary reaction involving an amine and the undesired nascent source of fatty acid. Thus, the methods disclosed herein provide an overall commercial-type process, beginning with the formation of the polyhydroxy amine, followed by its conversion into the polyhydroxy fatty acid amide (hereinafter "Primary Reaction"), optionally followed by the reduction (hereinafter "Secondary Reaction") in residual nascent fatty acid levels, especially if high sudsing is desired, since nascent fatty acids can reduce suds levels, followed by partial sulfation.

As an overall proposition, the preparative method described hereinafter will afford high quality N-alkylamino polyol reactants with desirable low Gardner Color and which are substantially free of nickel catalysts Such N-alkylamino polyols can then be reacted with, preferably, fatty acid methyl esters to provide high yields (90–98%) of polyhydroxy fatty acid amides having desirable low levels (typically, less than about 0.1%) of cyclized by-products and also with improved color and improved color stability, e.g., Gardner Colors below about 4, preferably between 0 and 2. The content of nascent fatty acids present in the polyhydroxy fatty acid amide is optionally minimized by the Secondary Reaction with amines, as disclosed herein. It will be understood that the nascent fatty acids are not thereby removed from the final product, but are converted into amido forms which can be tolerated in finished detergent compositions, even in liquid detergent compositions which contain calcium or magnesium cations. Indeed, by judicious selection of amines such as ethanolamine, the fatty acid monoethanolamides resulting from the secondary reaction are, themselves, desirable cleaning and suds-boosting ingredients, especially in liquid dishwashing detergents.

The following describes the reactants and reaction conditions for the overall process.

By "substantially water-free" or like terminology used herein is meant that all reactants, solvents, catalysts and apparatus are employed in as water-free state as is reasonably possible. Typically, solvents may be dried using molecular sieves; apparatus is swept dry with dry gas; reactants preferably contain the minimum possible amount of water. Typically, the moisture content of the reactants, solvents, etc., will be in the range of 0.2%, more preferably 0.1%, or less.

By "substantially free of nickel" herein is meant that the N-alkylamino polyol used in the primary reaction contains no more than about 20 parts per million (ppm) nickel, and preferably less than about 5 ppm nickel (Ni++). Nickel can be conveniently measured by conventional atomic absorption spectroscopy, using diluted samples (5/1 dilution to minimize interference).

By "reducible compounds" or "reducibles" herein is meant chemical compounds which contain reducing sugars either in their natural state or as an adduct with the amine such as N-methylglucamine. Such compounds include, but are not limited to, species such as glucose, fructose, maltose, xylose, N-methylglucosylamine, N-methylfructosylamine, N-methyl-N-glucosylglucamine. This is measured by g.c. analysis.

By "g.c. analysis" herein is meant gas-liquid chromatography ("g.l.c.") using Hewlett-Packard 5890 Series 2 on column injection using DB1 15 meter 0.25 /A film thickness ID 250 $\mu$.

By "improved color" and/or "improved color stability" herein is meant the Gardner Color of the N-alkylamino polyol reactant used in the present process. Moreover, the Gardner Color of the fatty amide surfactants which are subsequently made therefrom is also substantially improved.

By "Gardner Color" herein is meant the standard Gardner measurement known in the art. A Gardner Color reading near zero (solution) represents a nearly colorless ("water-white") solution. Gardner Colors in the 4–7 range are only marginally acceptable for the N-alkylamino polyol reaction products, and it is preferred to achieve Gardner Colors below about 4, preferably 0 to about 2. Of course, use of sugars having low Gardner Colors (e.g., 0 or 1, i.e., water-white syrups) will help ensure that N-alkylamino polyols having desirably low Gardner Colors will be produced. Stated otherwise, use of low (0–2) Gardner Color sugars (preferably white solids or water-white solutions) and use of the reaction sequence disclosed herein results in low Gardner Color N-alkylamino polyols (white or slightly off-white solids).

By "improved odor" herein is meant that the odor character of the reaction product is substantially free of amine or "fish" type odor (once any excess N-alkylamine is removed) and also substantially free of typical browning sugar odors.

By "nickel catalyst" herein is meant any of the conventional Raney nickel or "supported" nickel catalysts well-known in the art. Conventional nickel under the trademark RANEY NICKEL 4200 (Grace Chemicals) is quite suitable for use herein. RANEY NICKEL 3200, (United Catalyst, Inc.) UCI; G-96B and G-49A and G-49C are also suitable. While not intending to be limited by theory, it is believed that removing oxides of nickel from the catalyst prevents or impedes dissolution of nickel ions into the reaction milieu, and thus results in the formation of reaction products having a desirable low nickel content. Moreover, it has been found that the nickel catalyst pretreated with pressurized hydrogen can be re-used in multiple subsequent reactions, thereby yielding a substantial overall cost savings.

By "pressurized hydrogen" or "hydrogen pressure" in the polyhydroxy amine-forming reaction herein is meant: for treatment of the nickel catalyst typically 500 psig–5,000 psig; for reaction of the N-alkylamine and sugar (steps c and d below), typically 200 psig–5,000 psig.

By "sugars" in the polyhydroxy amine-forming reaction herein is meant reducing sugars such as glucose, fructose, mannose, lactose, maltose, xylose and the like. The term "sugars" herein also includes glyceraldehyde, although, as noted hereinafter, it may be simpler to use other reaction sequences in the manufacture of materials wherein Z=2. Such "sugars" include plant syrups such as cane syrups, corn syrups, potato starch-derived sugar syrups, hydrolyzed wood pulp-derived sugars and the like. High fructose, high glucose, high xylose and high maltose syrups are economical and preferred, especially if their Gardner Color is satisfactory.

By "N-alkylamines" in the polyhydroxy amine-forming reaction herein is meant compounds such as the N-methyl, N-ethyl, N-propyl, etc., $C_1$–$C_{10}$ N-alkylamines, and the corresponding hydroxysubstituted amines, e.g., ethanolamine. The $C_1$–$C_3$ alkylamines are preferred, and N-methylamine is most preferred.

By "amine reactant" in the secondary reaction to reduce fatty acid levels herein is meant, as noted above, $C_1$–$C_4$ amines and alkanolamines, examples of which include monoethanolamine (preferred), propylamine, ethylamine, 3-amino-1,2-propanediol, 1-amino-2-propanol, 3-amino-1-propanol, tris-(hydroxymethyl)aminoethane, 2-amino-2-ethyl-1,3-propanediol, ammonia, and the like.

By "free fatty acids" herein is meant the fatty acids per se, or salts thereof, e.g., sodium salts, i.e., soaps.

By "residual nascent source of fatty acids" herein is meant, for example, unreacted fatty acid ester starting materials, complex ester-amides which unavoidably form in small amounts during the primary reaction, and any other potential source of free fatty acid. It will be appreciated by the chemical formulator that during the overall reaction, work-up and storage of the polyhydroxy fatty acid amide surfactants, such nascent sources of fatty acids can break down in the presence of water in even modestly basic or acidic conditions to release the undesired fatty acids.

By "cyclized by-products" herein is meant the undesirable reaction by-products of the primary reaction wherein it appears that the multiple hydroxyl groups in the polyhydroxy fatty acid amides can form ring structures which are, in the main, not readily biodegradable. It will be appreciated by those skilled in the chemical arts that the preparation of the polyhydroxy fatty acid amides herein using the di- and higher saccharides such as maltose will result in the formation of polyhydroxy fatty acid amides wherein linear substituent Z (which contains multiple hydroxy substituents) is naturally "capped" by a polyhydroxy ring structure. Such materials are not cyclized by-products, as defined herein.

Formation of N-Alkylamino Polyol Raw Material

The preparation of the N-alkylaminol polyols used herein can be conducted in any well-stirred pressure vessel suitable for conducting hydrogenation reactions. In a convenient mode, a pressure reactor with a separate storage reservoir is employed. The reservoir (which, itself, can be pressurized) communicates with the reactor via suitable pipes, or the like. In use, a stirred slurry of the nickel catalyst is first treated with hydrogen to remove traces of nickel oxides. This can be conveniently done in the reactor. (Alternatively, if the manufacturer has access to an oxide-free source of nickel catalyst, pretreatment with $H_2$ is unnecessary. However, for most manufacturing processes some trace of oxides will inevitably be present, so the $H_2$ treatment is preferred.) After removal of excess slurry medium (water) the N-alkyl amine is introduced into the reactor. Thereafter, the sugar is introduced from the storage reservoir into the reactor either under hydrogen pressure or by means of a high pressure pumping system, and the reaction is allowed to proceed. The progress of the reaction can be monitored by periodically removing samples of the reaction mixture and analyzing for reducibles using gas chromatography ("g.c."), or by heating the sample to about 100° C. for 30–60 minutes in a sealed vial to check for color stability. Typically, for a reaction of about 8 liters (ca. 2 gallons) size the initial stage (to 95% of reducibles being depleted) requires about 60 minutes, depending somewhat on catalyst level and temperature. The temperature of the reaction mixture can then be raised to complete the reaction (to 99.9% of the reducibles being depleted).

In more detail, the process for preparing N-alkylamino polyols by reacting an N-alkylamine with a reducing sugar in the presence of a nickel catalyst under hydrogen pressure preferably will comprise:

(a) removing substantially all oxides of nickel from the nickel catalyst (conveniently, this can be done by contacting the nickel catalyst with hydrogen, typically under pressure and temperature of 50°–185° C. at 500–1,500 psig hydrogen);

(b) admixing the nickel catalyst from (a) with the N-alkylamine to provide mixture (b) under hydrogen pressure prior to admixture with the sugar;

(c) admixing the sugar with mixture (b) under hydrogen pressure;

(d) conducting the reaction of the sugar with the N-alkylamine/nickel catalyst mixture (b) at a temperature below about 80° C. and under hydrogen pressure (typically at least 250 psig, preferably at least 500 psig) until at least about 95% by weight of the reducible compounds are no longer present in the reaction mixture;

(e) continuing the reaction, optionally at a temperature of up to about 120° C., until at least about 99.9% by weight of the reducible compounds are no longer present in the reaction mixture; and (f) recovering the N-alkylamino polyol, preferably without purification.

A typical method is wherein the nickel catalyst level is in the range of from about 5% to about 50%, most typically about 10% to about 30%, by weight of the sugar reactants, for optimal throughput. Preferably step (d) is carried out at a temperature of from about 40° C. to about 70° C. Step (e) is preferably carried out at a temperature from about 80° C. to about 120° C. The catalyst may be used in repeat batches, as is.

The above process thus affords a convenient reaction for the preparation of compounds which include, but are not limited to, N-alkyl glucamine, N-alkyl fructamine, N-alkyl maltamine, N-alkyl xylamine, or N-alkyl glycerol amine, comprising the steps of:

(a) admixing a nickel catalyst which is substantially free of oxides of nickel with an N-alkylamine (preferably N-methylamine);

(b) under hydrogen pressure, admixing an aqueous solution of glucose, fructose, maltose or glyceraldehyde, respectively, with the mixture from step (a);

(c) allowing the mixture from step (b) to react at a temperature of from about 40° C. to about 70° C. until at least about 95% by weight of the reducible compounds are no longer present in the reaction mixture; and (d) allowing the reaction from step (c) to continue at a temperature below about 120° C. until at least about 99.9% by weight of the reducible compounds are no longer present in the reaction mixture.

Preferably the process is conducted with said catalyst being present at the 10% to 30% level relative to sugar.

When preparing 1,2-propanediol derivatives (e.g., N-alkyl glycerol amines) the formulator may elect to react an N-alkylamine with, for example, 3-chloro-1,2-propanediol or glycidol, at room temperature to about 65° C., typically in ethanol or water.

Primary Reaction to Form Polyhydroxy Fatty Acid Amides

The primary reaction herein for preparing polyhydroxy fatty acid amide surfactants, comprises reacting a member selected from the group consisting of, preferably, fatty acid esters with an N-alkylamino polyol. In a preferred method, the fatty acid ester is a $C_{10}$–$C_{18}$ alkyl or alkenyl fatty acid methyl ester and the N-alkylamino polyol is selected from N-methyl glucamine, N-methyl fructamine, N-methyl maltamine, N-methyl xylamine and N-methyl glycerol amine.

The amide-forming primary reaction herein can be illustrated by the formation of N-lauroyl N-methyl glucamine, as follows.

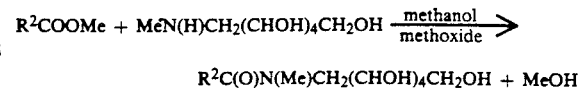

$R^2C(O)N(Me)CH_2(CHOH)_4CH_2OH + MeOH$ wherein $R^2$ is $C_{11}H_{23}$ alkyl.

More generally, the process herein can be used to prepare polyhydroxy fatty acid amide surfactants of the formula:

(I)

wherein: $R^1$ is H, $C_1$-$C_4$ hydrocarbyl, 2-hydroxyethyl, 2-hydroxypropyl, or a mixture thereof, preferably $C_1$-$C_4$ alkyl, more preferably $C_1$ or $C_2$ alkyl, most preferably $C_1$ alkyl (i.e., methyl); and $R^2$ is a $C_5$-$C_{31}$ hydrocarbyl moiety, preferably straight chain $C_7$-$C_{19}$ alkyl or alkenyl, more preferably straight chain $C_9$-$C_{17}$ alkyl or alkenyl, most preferably straight chain $C_{11}$-$C_{19}$ alkyl or alkenyl, or mixture thereof; and Z is a polyhydroxyhydrocarbyl moiety having a linear hydrocarbyl chain with at least 2 (in the case of glyceraldehyde) or 3 hydroxyls (in the case of other reducing sugars) directly connected to the chain, or an alkoxylated derivative (preferably ethoxylated or propoxylated) thereof. Z preferably will be derived from a reducing sugar in a reductive amination reaction; more preferably Z is a glycityl moiety. Suitable reducing sugars include glucose, fructose, maltose, lactose, galactose, mannose, and xylose, as well as glyceraldehyde. As raw materials, high dextrose corn syrup, high fructose corn syrup, and high maltose corn syrup can be utilized as well as the individual sugars listed above. These corn syrups may yield a mix of sugar components for Z. It should be understood that it is by no means intended to exclude other suitable raw materials. Z preferably will be selected from the group consisting of —$CH_2$—$(CHOH)_n$—$CH_2OH$, —$CH(CH_2OH)$—$(CHOH)_{n-1}$—$CH_2OH$, —$CH_2$—$(CHOH)_2(CHOR')$—$(CHOH)$—$CH_2OH$, where n is an integer from 1 to 5, inclusive, and R' is H or a cyclic mono- or poly- saccharide, and alkoxylated derivatives thereof. Most preferred are glycityls wherein n is 4, particularly —$CH_2$—$(CHOH)_4$—$CH_2OH$.

In Formula (I), $R^1$ can be, for example, N-methyl, N-ethyl, N-propyl, N-isopropyl, N-butyl, N-isobutyl, N-2-hydroxy ethyl, or N-2-hydroxy propyl.

$R^2$-CO-N< can be, for example, cocamide, stearamide, oleamide, lauramide, myristamide, capricamide, palmitamide, tallowamide, etc.

Z can be 1-deoxyglucityl, 2-deoxyfructityl, 1-deoxyxylityl, 1-deoxymaltityl, 1-deoxylactityl, 1-deoxygalactityl, 1-deoxymannityl, 1-deoxymaltotriotityl, 2,3-dihydroxypropyl (from glyceraldehyde), etc.

The following reactants, catalysts and solvents can conveniently be used herein, and are listed only by way of exemplification and not by way of limitation.

Reactants—As noted above, various fatty ester reactants can be used herein, but fatty methyl esters are most preferred. Various other fatty esters can be used in the primary reaction, including mono-, di- and triesters (i.e., triglycerides). Methyl esters are convenient and commercially available with low Gardner Color, and ethyl esters, and the like are all quite suitable. The polyhydroxyamine reactants include N-alkyl and N-hydroxyalkyl polyhydroxyamines with the N-substituent group such as $CH_3$—, $C_2H_5$—, $C_3H_7$—, $HOCH_2CH_2$—, and the like. As noted above, such materials preferably are substantially free of nickel catalysts. Mixtures of the ester and mixtures of the polyhydroxyamine reactants can also be used.

Catalysts—The catalysts used in the primary reaction are basic materials such as the alkoxides (preferred), hydroxides—if provision is made to remove water from them and polyhydroxyamine prior to addition of ester—carbonates, and the like. Preferred alkoxide catalysts include the alkali metal $C_1$-$C_4$ alkoxides such as sodium methoxide, potassium ethoxide, and the like. The catalysts can be prepared separately from the reaction mixture, or can be generated in situ using an alkali metal such as sodium. For in situ generation, e.g., sodium metal in the methanol solvent, it is preferred that the other reactants not be present until catalyst generation is complete. The catalyst typically is used at 0.1-10, preferably 0.5-5, most preferably 5 mole percent of the ester reactant. Mixtures of catalysts can also be used.

Solvents—The organic hydroxy solvents used in the primary reaction include methanol, ethanol, glycerol, 1,2-propanediol, 1,3-propylene glycol, and the like. Methanol is a preferred alcohol solvent and 1,2-propanediol (propylene glycol) is a preferred diol solvent. Mixtures of solvents can also be used.

General Reaction Conditions—As noted, it is desired to prepare the products of the primary reaction (amidation) while minimizing the formation of cyclized by-products, ester amides and color bodies. Reaction temperatures below about 135° C., typically in the range of from about 40° C. to about 100° C., preferably 60° C. to 90° C., are used to achieve this objective, especially in batch processes where reaction times are typically on the order of about 90 minutes, or even up to 3 hours. Most preferably, this reaction is conducted at 85° C. Somewhat higher temperatures can be tolerated in continuous processes, where residence times can be shorter. All reactants, catalysts, solvents, etc. should be substantially dry. For example, the fatty esters and N-methyl glucamine preferably contain less than about 0.1% water. The concentration ranges of the reactants and solvent provide, for example, what can be termed a "70% concentrated" (with respect to reactants) reaction mixture. This 70% concentrated mixture provides excellent results, in that high yields of the desired polyhydroxy fatty acid amide product are secured rapidly. Indeed, indications are that the reaction is substantially complete within one hour, or less. The consistency of the reaction mixture at the 70% concentration level provides ease of handling. Even better results are secured at the 80% and 90% concentration levels. However, at the higher concentrations the reaction systems are somewhat more difficult to work with, and require more efficient stirring (due to their thickness), and the like, at least in the early stages of the reaction. Once the reaction proceeds to any appreciable extent, the viscosity of the reaction system decreases and ease of mixing increases. In one mode, product yields can be increased a few percent by allowing the reaction mixture to "age" (even to solidify) a few hours or days to allow final traces of starting materials to react at lower temperatures.

EXAMPLE I

Preparation of Polyhydroxyamine

Catalyst Treatment—Approximately 300 mls of RANEY NICKEL 4200 (Grace Chemicals) is washed with deionized water (1 liter total volume; 3 washings) and decanted. The total catalyst solids can be determined by the volume-weight equation provided by Grace Chemicals, i.e., [(total wt. catalyst+water)−(water wt. for volume)]×7/6=Nickel solids.

308.21 g. of the catalyst Ni solids basis are loaded into a 2 gallon reactor (316 stainless steel baffled autoclave with DISPERSIMAX hollow shaft multi-blade impeller from Autoclave Engineers) with 4 liters of water. The reactor is heated to 130° C. at 1400–1600 psig hydrogen for 50 minutes. The mixture is cooled to room temperature at 1500 psig hydrogen and left overnight. The water is then removed to 10% of the reactor volume using an internal dip tube.

Reaction—The reactants are as follows. 881.82 mls. 50% aqueous monomethylamine (Air Products, Inc.; Lot 060–889–09); 2727.3 g. 55% glucose syrup (Cargill; 71% glucose; 99 dextrose equivalents; Lot 99M501).

The reactor containing the $H_2O$ and Raney nickel prepared as noted above is cooled to room temperature and ice cold monomethylamine is loaded into the reactor at ambient pressure with $H_2$ blanket. The reactor is pressurized to 1000 psig hydrogen and heated to 50° C. for several minutes. Stirring is maintained to assure absorption of $H_2$ in solution.

The glucose is maintained in a separate reservoir which is in closed communication with the reactor. The reservoir is pressurized to 4000 psig with hydrogen. The glucose (aqueous solution) is then transferred into the reactor under $H_2$ pressure over time. (This transfer can be monitored by the pressure change in the reservoir resulting from the decrease in volume of the sugar solution as it is transferred from the reservoir into the main reactor. The sugar can be transferred at various rates, but a transfer rate of ca.100 psig pressure drop per minute is convenient and requires about 20 minutes for the volume used in this run.) An exotherm occurs when the aqueous sugar solution is introduced into the reactor; the 50° C. internal temperature raises to ca. 53° C.

Once all the glucose has been transferred to the reactor the temperature is maintained at 50° C. for 30 minutes. Hydrogen uptake is monitored by a pressure gauge. Stirring is continued throughout at 800–1,100 rpm or greater.

The temperature of the reactor is increased to 60° C. for 40 minutes, then to 85° C. for 10 minutes, then to 100° C. for 10 minutes. The reactor is then cooled to room temperature and maintained under pressure overnight. The reaction product dissolved in the aqueous reaction medium is conveniently recovered by using an internal dip tube with hydrogen pressure. Particulate nickel can be removed by filtration. Preferably, an internal filter is used to avoid exposure to air, which can cause nickel dissolution. Solid N-methyl glucamine is recovered from the reaction product by evaporation of water.

The foregoing procedure can be repeated using fructose as the sugar to prepare N-methyl fructamines.

The foregoing procedure can also be repeated using glyceraldehyde as the sugar to prepare N-methyl glycerol amine (3-methylamino-1,2-propanediol).

Conversion of Polyhydroxy Amine to Polyhydroxy Fatty Acid Amide Surfactant Reaction Product and Minimization of Nascent Fatty Acids by the Secondary Reaction As the initial step, the substantially water-free N-methyl glucamine prepared above is reacted with fatty acid methyl esters to prepare the corresponding fatty acid amides of N-methyl glucamine in the manner disclosed above and in the experimental details, hereinafter. It will be appreciated that coconut fatty acid methyl esters, palm oil fatty acid esters, tallow fatty acid esters, oleyl esters, polyunsaturated fatty acid esters, and the like, can all be used in this reaction, and various N-alkyl polyols, e.g., N-methyl fructamine, N-methyl maltamine, etc., can be used in place of the N-methyl glucamine.

The secondary reaction can thereafter be carried out using primary alkyl amines and alkanolamines. However, it will be appreciated by the chemist that, since alkyl amines generally have undesirable odors, as compared with alkanolamines, it is preferred to employ the alkanolamines. By so doing, removal of traces of unreacted amine material from the final product of the process is unnecessary, since products with improved odor are secured.

Moreover, while secondary amines will function adequately in the process herein to remove the nascent sources of fatty acids, such amines can undesirably form nitrosamines. Accordingly, the primary amines, especially the primary alkanolamines such as ethanolamine ("mono-ethanolamine") are much preferred for use in the secondary reaction herein.

It will be further appreciated that it is desirable that the secondary reaction herein be carried out quickly, such that decomposition of the desired polyhydroxy fatty acid amide surfactant is kept to a minimum. In essence, the secondary reaction is an amidation reaction, and seems to be potentiated and accelerated by having a solvent supportive of nucleophilic reaction present. Since methanol is such a solvent, and is also one of the preferred solvents for use in the primary reaction herein, it suffices quite well to also act as the solvent for the secondary reaction. Preferably, at least about 6–8% by weight of such solvent which is supportive of nucleophilic reactions, especially methanol, is used in the secondary reaction of this invention, as well as some 1,2-propanediol. 1,2-propanediol, alone, can also serve as the solvent for the secondary reaction, but does not appear to be quite as effective as when methanol is present. Other lower alcohols, such as ethanol and isopropanol, could also be used, but may be poorer choices than methanol or mixtures of methanol/1,2-propanediol. Under such circumstances, some minimal loss (ca. about a 1% decrease in overall yield) of polyhydroxy fatty acid amide surfactant may be unavoidable, but this is usually an acceptable trade-off for the desired decrease in fatty acids in the final product.

The reaction temperature for the secondary reaction should preferably be about 85° C., or below, typically in the 65° C.-85° C. range. It will be appreciated that use of excessively high temperatures may desirably speed the secondary reaction, but will undesirably begin to cause cyclization of the polyhydroxy fatty acid amides. While temperatures up to about 120° C. might be tolerable for short periods of time, it would, of course, be undesirable to decrease nascent fatty acid content at the expense of increasing the level of cyclized by-product. The following further illustrates the Primary Reaction followed by the Secondary Reaction.

Apparatus: 500 ml three necked flask, paddle stirrer, reflux condenser with drying tube, thermometer reaching into reaction and a gas inlet tube. The flask is heated with a thermostatted oil bath.

Primary Reaction

The apparatus is predried under nitrogen sweep, cooled and the sweep is shut off. A tare weight is taken without the condenser. Pure powdered N-methylglucamine ("NMG") 97.5 g (0.5 mole), 107 g (0.5 mole) 95% methyl dodecanoate and 18.9 g propylene glycol (solvent) are placed into the flask; the moisture content of each reactant is, respectively, 0.3% and 0.1%, and the solvent is dried over molecular sieves. The mixture is heated to 68° C. with stirring to give a viscous paste; 5.4 g (0.025 mole) 25% sodium methoxide in methanol is then added. The time is taken as zero, and the reaction then brought quickly to 85° C., and held at 85° C. with continuous stirring, no vacuum, no nitrogen sweep. Within 5 minutes a thin milky suspension is formed which clears to a homogeneous clear low viscosity liquid at 55 minutes. During this reaction no reflux is observed, although methanol evolution is calculated to reach 9.1% at complete amidation with NMG. At 150 minutes, the weight of the reaction is within 2 g of initial; a small sample is taken.

In an alternate mode, various surfactants, especially nonionic surfactants such as the ethoxylated alcohols (NEODOL), as well as alkyl glycosides and preformed polyhydroxy fatty acid amides, can be present in the reaction mixture (typically 5-30%) to help provide a single phase mixture.

Secondary Reaction

Immediately following the Primary Reaction, 7.6 g (0.125 mole) of dry ethanolamine is added. Vacuum/nitrogen sweep is then applied as stirring and temperature are maintained. At the 210 minute point the vacuum reaches 11 psi (4 psi absolute). Weighing indicates about 1.5 to 2% of reaction weight in excess of theoretical removal of all methanol from catalyst and ester. The resulting product has the following analysis and is suitable for use in high sudsing detergent compositions.

|  | Calculated GC Area % | Concentrations |
|---|---|---|
| Methyl ester | 0.1% | 0.1% |
| Fatty acid/soap | 0.3% | 0.2% |
| NMG | 6.5% | 5.5% |
| Monoethanol amide | 2.6% | 2.2% |
| Total glucoseamide | 89.9% | 76.4% |
| $C_{10}$ | 1.1% | 0.9% |
| $C_{12}$ | 87.6% | 74.5% |
| $C_{14}$ | 1.2% | 1.0% |
| Ester amide | 0.1% | 0.1% |
| Assumed components not observed in GC |  |  |
| Propylene glycol |  | 10.0% |
| Methanol |  | 2.0% |
| Monoethanolamine |  | 3.0 |
| TOTAL |  | 99.5% |

The sugar-derived polyhydroxy fatty acid amides used herein have a linear hydrcarbyl chain Z containing at least three hydroxyl groups and are generally prepared as noted above. For polyhydroxy fatty acid amides derived from glycerol, hydrocarbyl chain Z contains two hydroxyl groups, and the reaction sequence for their preparation can optionally be somewhat different, as noted below. Such materials are formally named as N-(1,2-propanediol) fatty acid amides, and are provided by various reaction sequences, as noted hereinafter.

Sequence A:

$CH_3NH_2 + ClCH_2CH(OH)CH_2OH \longrightarrow$

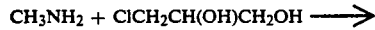

$CH_3NHCH_2CH(OH)CH_2OH$ ("MAPD")

Sequence B:

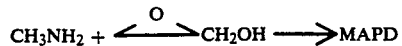

$CH_3NH_2 +$  $CH_2OH \longrightarrow MAPD$

Sequence A or B can be used when the alkyl substituent present on the amine reactant contains a hydroxyl group, e.g., monoethanolamine.

The amide surfactants used herein are then conveniently prepared by reacting the glycerol-amine prepared as noted above with a $C_8-C_{20}$ fatty acid ester (e.g., methyl, ethyl, etc. ester) typically in the presence of an alkoxide catalyst and alcohol and/or 1,2-propanediol solvent, as illustrated by the following.

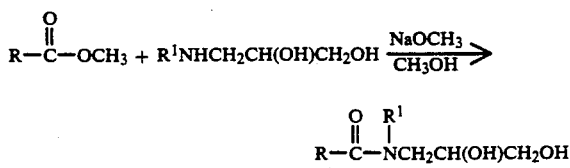

wherein R is typically $C_7-C_{21}$ alkyl or alkenyl and $R^1$ is typically $C_1-C_4$ alkyl, hydroxyalkyl, or alkenyl, preferably methyl ($-CH_3$) or hydroxyethyl ($-CH_2CH_2OH$). The examples hereinafter illustrate these reactions in greater detail.

In yet another mode, the preparation of the N-(1,2-propanediol) fatty acid amides can be conducted by reacting glyceraldehyde with an alkyl amine under hydrogen, with Ni catalyst, followed by reaction of the resulting N-alkyl-1,2-propanediol amine with a fatty ester in a solvent such as methanol or 1,2-propanediol solvent in the presence of a base catalyst such as sodium methoxide. A pressure reactor with a separate storage reservoir is typically employed. The reservoir (which can be pressurized) communicates with the reactor via suitable pipes, or the like. In use, a stirred slurry of a nickel catalyst (Raney Nickel 4200; Grace Chemicals) is first treated with hydrogen to remove traces of nickel oxides. This can be done in the reactor at about 50° C., 1,000 psig hydrogen. (If the manufacturer has access to an oxide-free source of nickel catalyst, pretreatment with $H_2$ is unnecessary. However, for most manufacturing processes some trace of oxides will inevitably be present, so the $H_2$ treatment is preferred.) After removal of excess slurry medium (water) the N-alkyl amine is introduced into the reactor. Thereafter, the glyceraldehyde is introduced from the storage reservoir into the reactor either under hydrogen pressure or by means of a high pressure pumping system, and the reaction is allowed to proceed at about 60°-85° C. and 2,000 psig hydrogen for about an hour. The progress of the reaction can be monitored by periodically removing samples of the reaction mixture and analyzing for reducibles using gas chromatography ("g.c."), or by heating the sample to about 100° C. for 30-60 minutes in a sealed vial to check for color stability. Typically, for a reaction of about 8 liters (ca. 2 gallons) size the initial stage (to 95% of reducibles being depleted) requires about 60 minutes, depending somewhat on catalyst level and temperature. The temperature of the reaction mixture can then be raised to complete the reaction (to 99.9% of the reducibles being depleted). After removal of water, the N-alkyl-1,2 propanediol amine thus prepared is then admixed with a fatty acid methyl ester (e.g., coconutalkyl methyl ester) at a 1:1 mole ratio in 1,2-propanediol solvent and with sodium methoxide, and allowed to react for about 4 hours at 70° C. to provide the amide surfactant. The following Examples illustrate this more fully.

EXAMPLE II

Preparation of HEAPD and Reaction with Methyl Laurate

Step 1: Reaction of glycidol (50.0 g) with ethanolamine (45.32 g; Aldrich) to prepare 3-[2-(hydroxyethyl)amino]-1,2-propanediol ("HEAPD").

Glycidol is added under nitrogen to a cooled stirring solution of neat ethanolamine. The rate of addition is adjusted to keep the solution below 20° C. After half of the glycidol is added the reaction mixture becomes so viscous that stirring stops. Ethanol (47.5 g, 50 wt. %) is added and the addition of glycidol is continued; the reaction is allowed to warm slowly to room temperature. The ethanol and unreated ethanolamine are removed by vacuum distillation. The product does not distill at 130° C. (internal temperature) under full vacuum, so the pale yellow hazy liquid is used directly in further reactions. Characterization by TLC (80 $CHCl_3$:23 MeOH:3 $NH_4OH$) showed two products. The desired HEAPD amine can be purified by Kugelrohr distillation at 165°-175° C., and characterized by $C_{13}$ n.m.r. and GC.

Step 2: The HEAPD prepared in the foregoing manner (13.5 g) is reacted with methyl laurate (P&G CE 1295; 21.4 g) to provide the corresponding amide, as follows.

The HEAPD amine, the ester, methanol (3.5 g, 10 wt. %) and sodium methoxide (2.16 g, 10 mole%) are mixed in a small jar. A stirbar is added and the jar is sealed. The reaction is heated to (70°-75° C.) in an oil bath with stirring. About 5 minutes after the mixture is completely heated the two phases mix and slowly become clear. The mixture is cooled, poured into an evaporating dish, and dried in a vacuum oven. TLC after 5 hours of drying shows unreacted ester in about the same ratio as amide, but no free amine. The desired amide product is precipitated from acetone and is redried.

The following Examples III(A)-III(E) illustrate the preparation of 3-methylamino-1,2-propanediol (MAPD) and the reaction of MAPD or HEAPD with fatty acid esters for use herein.

EXAMPLE III (a) Preparation of MAPD from 100 g 3-chloro-1,2-propanediol (Aldrich) and 351.2 g monomethylamine (MMA; 40% in water; Aldrich).

The chlorodiol is added to the amine at room temperature and the reaction is run without cooling. After 20 minutes the temperature is at 64° C. After 5 hours the reaction cools back to room temperature, and the excess MMA and water are removed at 60° C. on a rotovap. The product is dissolved in methanol and sodium methoxide (50%) is added to bring the pH to 11.3. After sitting for 5 hours, NaCl precipitate is filtered off. The product solution is evaporated (rotovap) to give a solid as a semi-liquid. Characterized by IR and $C_{13}$ n.m.r.

(b) Preparation of MAPD from 185.2 g glycidol (Aldrich) and 1176.7 g MMA (33% in ethanol; Fluka).

Glycidol is added to a cooled (ice water bath, solution at 1 C) stirring solution of MMA. The glycidol is added over 1 hour to ensure that the temperature does not exceed 20° C. The reaction is kept in an ice bath for 2 ½ hours and then allowed to warm to room temperature overnight. The ethanol is removed on the rotovap and the product is purified by kugelrohr distillation at 120° C. to give a clear viscous liquid. Characterized by GC (99%) and $C_{13}$ n.m.r.

(c) Preparation of MAPD from 50.0 g glycidol and 78.28 g MMA (40% in water; Aldrich).

Glycidol is added to a cooled (ice water bath, solution at 7° C.) stirring solution of MMA. The glycidol is added over 2 hours with care so that the reaction remains below 20° C. The solution is kept in the ice bath for I hour and then the water is removed at 85° C. for 1 hour on the rotovap. 50 mL of methanol are added and then are removed on the rotovap. The product is purified by kugelrohr distillation at 115°-125° C. to give a clear viscous liquid; characterization is by G.C. and n.m.r.

(d) Preparation of hardened tallow amide of MAPD from 10.51 g 3-methylamino-1,2-propanediol (MAPD) and 28.83 g hardened tallow methyl ester.

The ester is melted with stirring in a sealed jar. After 3-4 minutes' cooling, the MAPD, methanol (2.16 g, 0.068 mole, 10 wt. %) and sodium methoxide (2.16 g, 25% in MEOH, 10 mole %) are added. The resealed jar is heated to 78° C. in an oil bath. After 20 minutes, the hazy mixture clears and the jar is removed from the oil bath. The reaction mixture solidifies overnight and the product is dried in a vacuum oven and ground to give a waxy solid. Characterization is done by IR and TLC, GC and $C_{13}$ n.m.r.

(e) Preparation of hardened tallow amide of HEAPD from 20.25 g 3-hydroxyethylamino-1,2-propanediol (HEAPD) and 38.88 g hardened tallow methyl ester.

The HEAPD, ester, methanol (6.2 g, 0.19 mole, 10 wt. %) and sodium methoxide (2.92 g of 25% solution in methanol, 10 mol %) are mixed in a jar. A stirbar is added and the jar is sealed. The reaction is heated to reflux (75° C.) with stirring in an oil bath. The reaction clears once at temperature (20 minutes) except for solid HEAPD. An additional 5 minutes of heating is used to dissolve all of the amine, and then the jar is removed from the oil bath. The pale yellow solution begins to solidify after 30 minutes and is completely solid after sitting overnight. The product is dried in a vacuum oven and ground to give a waxy solid. Characterization is by GC and n.m.r. spectroscopy.

SULFATION REACTION

It is to be understood that the sulfation products herein are believed to be mainly monosulfates on the terminal hydroxyl substituent of the polyhydroxy fatty acid amides. However, since the amides do contain multiple hydroxyl groups where sulfation can occur, the di-, tri-, tetra-, etc. sulfates can be formed in varying amounts and be co-present in the compositions. Indeed, it appears that using the syntheses disclosed herein, approximately 10% di-sulfation can routinely occur. The presence of such polysulfated materials does not detract from the performance herein, and no special purification steps need be used to remove them.

EXAMPLE IV

Step 1—Two hundred grams of the $C_{12-14}$ N-methyl glucamide are dissolved in one liter of methylene chloride and transferred to a 2 l reaction flask. Step 1—66.8 grams of a 1:1 (mole basis) pyridine/$SO_3$ complex obtained from Aldrich Chemical Company are added to the reaction flask. The reaction is allowed to proceed at room temperature for three days (a matter of convenience; other reaction times can be used, depending on temperature, etc. ). Step 3—25 grams of sodium carbonate are dissolved in 80 mls. water and added to the reaction flask with mixing for four hours. Step 4—The crude reaction mixture is evaporated and the residue taken up in methanol (total volume 1.4 l). Step 5—The methanol is dried over MgSO₄ and the solids removed by vacuum filtration. Step 6—The methanol solution is decolorized with charcoal; the charcoal is removed by filtration through a Celite bed. Step 7—Excess methanol is evaporated on a rotary evaporator (60° C.; vacuum). The residue is slurried with ethyl acetate (slightly warm). Step 8—The ethyl acetate slurry is cooled to room temperature and the solids allowed to settle. The ethyl acetate containing the desired sulfated glucamide surfactant is decanted from the solids and the solvent removed by evaporation. Step 9—The solids remaining after evaporation of the ethyl acetate are ground by mortar and pestle and dried in a vacuum oven (25° C.; 20 mm pressure). The yield is 205 g/84.7% of theoretical.

EXAMPLE V

Tallow ($C_{16}$-$C_{18}$) N-methylglucamide is sulfated similarly, except that pyridine is used in place of methylene chloride as the solvent in the first step. A precipitate forms in Step 5, and is removed by filtration. The sulfated tallow N-methyl glucamide requires no decolorization.

Mg/Ca Salts

The sulfated polyhydroxy fatty acid amide surfactants herein are conventionally prepared in their acid or alkali metal (e.g., Na, K) salt forms, or as ammonium or alkanolammonium salts, e.g., triethanolammonium. These counterion salts are non-limiting examples of typical sulfated detergents. However, in circumstances where high grease removal performance is of particular importance, the formulator may find it advantageous to incorporate at least about 0.5%, preferably from about 0.6% to about 2%, by weight of magnesium ions, calcium ions, or mixtures thereof, into the finished detergent composition. This can be done by simply adding various water-soluble salts such as the chlorides, sulfates, acetates, etc. of magnesium or calcium to the compositions. It is also useful to generate the magnesium and/or calcium salts of the sulfated polyhydroxy fatty acids herein by reacting Mg(OH)₂ or Ca(OH)₂ with the acid form of the sulfated polyhydroxy fatty acid amide, and this can conveniently be done in situ during the formulation of the finished detergent compositions or as a separate step during the manufacture of the sulfated surfactant, itself.

Low Sudsing Compositions

Under some circumstances the formulator of detergent compositions may find it desirable to provide low sudsing compositions. For example, low sudsing is a desirable feature of window cleaners, floor and wall cleansers, and other hard surface cleansers where excess sudsing would require inconvenient rinsing steps in the overall cleaning process. Dishwashing detergents for use in automatic machines must be formulated to have essentially no suds, since excess suds can actually spill out of the machines. Likewise, European-style front loading fabric washing machines require low sudsing detergents to avoid suds spillage. Low sudsing can also be advantageous in concentrated laundering processes such as described in U.S. Pat. Nos. 4,489,455 and 4,489,574.

It transpires that the polyhydroxy fatty acid amides of formula (I) herein having H, hydroxyalkyl and/or methyl or ethyl substituents as group $R^1$ are high sudsers, whereas the compounds with $R^1$ as $C_3$-$C_8$ (straight-chain, branched chain or cyclic) are low sudsers. Importantly for cleaning purposes, the low sudsers still lower interfacial tensions very substantially and are thus quite active detersive surfactants.

Accordingly, when formulating low sudsing compositions herein the formulator may wish to employ compounds of formula (II), conveniently and preferably with their corresponding sulfates,

(II)

wherein $R^2$ and Z are as in formula (I), above, and wherein $R^1$ is $C_3$ to about $C_8$ alkyl, e.g., propyl, butyl, isopropyl, pentyl, cyclopentyl, n-hexyl (preferred), cyclohexyl, and also including various alkyl-branched substituents such as 2-ethylhexyl, and the like. Alternatively, the sulfates with shorter alkyl chains, disclosed above, can be used with these longer chain polyhydroxy fatty acid amides, but this is less convenient from a manufacturing standpoint. The synthesis of such compounds follows the steps noted above. Of course, for low sudsers the formulator may opt not to conduct the hereinbefore described steps ("Secondary Reaction") to diminish the levels of fatty acids in the reaction products, since the fatty acids can, themselves, help control suds.

By "low sudsing" herein is meant a suds height or suds volume for the low sudsing detergent compositions herein containing the $C_3$-$C_8$ N-alkyl polyhydroxy fatty acid amide surfactant which is substantially less than that which is achieved in comparable compositions containing the N-methyl polyhydroxy fatty acid amide surfactant. Typically, the compositions herein provide average sudsing which is no greater, on average, than about 70%, preferably no greater than about 50%, of that produced with the N-methyl surfactants. Of course, the sudsing can be still further reduced by means of standard suds control agents such as the silicones, various fatty materials and the like.

For the convenience of the formulator, a useful test procedure for comparing the sudsing of the low-suds compositions herein is provided hereinafter. The test comprises agitating aqueous solutions containing the detergent being tested in a standardized fashion and comparing sudsing against equivalent detergents containing the N-methyl polyhydroxy fatty acid amide. This particular test is run at ambient temperature (ca. 23° C.) and at 60° C., and at water hardness (3:1 Ca:Mg) levels of 10.4 gr/gal (178 ppm) and 25 gr/gal (428 ppm) to mimic a wide variety of prospective usage conditions. Of course, the formulator may modify the test conditions to focus on prospective usage conditions and user habits and practices throughout the world.

Sudsing Test

Suds cylinders having the dimensions 12 inch (30.4 cm) height and 4 inch (10.16 cm) diameter are releasably attached to a machine which rotates the cylinders 360° around a fixed axis. A typical test uses four cylinders, two for the standard comparison detergent product and two for the low sudsing detergent test product.

In the test, 500 mL of aqueous solution of the respective detergents is placed in the cylinders. Conveniently, the solutions comprise 3 g of the detergent, but other amounts can be used. The temperature of the solutions and their hardness is adjusted as noted above. Typically, $CaCl_2$ and $MgCl_2$ salts are used to supply hardness. The cylinders are sealed and the 500 ml level marked with tape. The cylinders are rotated through two complete revolutions, stopped and vented.

After the foregoing preparatory matters have been completed, the test begins. The cylinders are allowed to rotate 360° on the machine at a rate of 30 revolutions per minute. The machine is stopped at one minute intervals, the suds height from the top of the solution to the top of the suds is measured. The machine is restarted. The test proceeds thusly for 10 minutes. A suds "volume" is calculated by taking the average suds height over the test time (10 minutes) and can be expressed as suds volume per minute (cm), which conforms with: suds volume per minute = sum of suds height at each time of measurement divided by total time (10 minutes).

It is to be understood that the forgoing test provides a relative comparison between low sudsing detergent compositions of the type provided herein vs. standard comparison products. Stated otherwise, absolute values of suds heights are meaningless, since they can vary widely with solution temperature and water hardness. As a reasonable point of comparison, the low sudsing compositions herein yield approximately one-half the suds of the high sudsers at ambient temperature and water hardness of 10.4.

The sulfated polyhydroxy fatty acid amides prepared in the manner of this invention can be used as is in detergent compositions which comprise the typical detersive builders, enzymes, bleaches, soil release agents, and the like. Typically, at least about 5%, preferably 5% to 30% by weight of the sulfated polyhydroxy fatty acid amide can be used in such compositions. In a preferred mode, a 10:1 to 1:10 mixture of said sulfated amide and its unsulfated counterpart polyhydroxy fatty acid amide are used to provide a mixed nonionic/anionic surfactant system. Such mixtures are typically used at 1:3 to 3:1, preferably about 1:1 ratios. Mixtures with soaps are also useful for lowering interfacial tensions.

What is claimed is:

1. A method for sulfating a polyhydroxy fatty acid amide, comprising contacting said polyhydroxy fatty acid amide with an $SO_3$/pyridine complex in a non-hydroxy solvent at a reaction temperature from about 25° C. to about 35° C. to produce a yield of at least about 80% of a sulfated polyhydroxy fatty acid amide.

2. A method according to claim 1 wherein the reaction is carried out in a solvent which is a member selected from methylene chloride and pyridine, whereby the yield of sulfated polyhydroxy fatty acid amide is at least about 80%, by weight.

* * * * *